United States Patent [19]
Cocuzza et al.

[11] 3,935,279
[45] Jan. 27, 1976

[54] PROCESS FOR THE PRODUCTION OF GLYCOL ETHERS

[75] Inventors: Gioacchino Cocuzza, Catania; Benedetto Calcagno, Milan; Gianni Torreggiani, Varese, all of Italy

[73] Assignee: Societa'Italiana Resine S.I.R. S.p.A., Milan, Italy

[22] Filed: Dec. 26, 1973

[21] Appl. No.: 428,575

[30] Foreign Application Priority Data
Dec. 22, 1972 Italy.................................. 33441/72

[52] U.S. Cl. ......................... 260/615 R; 260/615 B
[51] Int. Cl.² ........................................ C07C 41/02
[58] Field of Search ......................... 260/615 B, 615

[56] References Cited
UNITED STATES PATENTS

| | | | |
|---|---|---|---|
| 1,696,874 | 12/1928 | Young............................. | 260/615 R |
| 2,276,597 | 3/1942 | Stanley............................ | 260/615 B |
| 2,870,220 | 1/1959 | Carter............................. | 260/615 B |
| 3,489,690 | 1/1970 | Lachampt et al. ............... | 260/615 B |

*Primary Examiner*—Howard T. Mars
*Attorney, Agent, or Firm*—Sughrue, Rothwell, Mion, Zinn & Macpeak

[57] ABSTRACT

A process for the production of ethylene glycol ethers by reacting ethylene oxide with monofunctional aliphatic alcohols, which comprises
  reacting a monofunctional aliphatic alcohol and ethylene oxide in a first reaction stage in a molar ratio of from about 3:1 to 20:1;
  separating excess alcohol from the ethylene glycol ethers obtained as the reaction products in the first stage;
  reacting the ethylene glycol ethers with ethylene oxide in a molar ratio of from about 1:1 to 10:1 and with monoethylene glycol ether in a second reaction stage;
  separating the monoethylene glycol ether and the diethylene glycol ether from the reaction products of the second stage, maintaining a weight ratio of the discharged fraction to the recycled fraction of from about 0.5:1 to 5:1.

The reaction is carried out under abiabatic conditions in the first stage and under isothermal conditions in the second stage.

7 Claims, 1 Drawing Figure

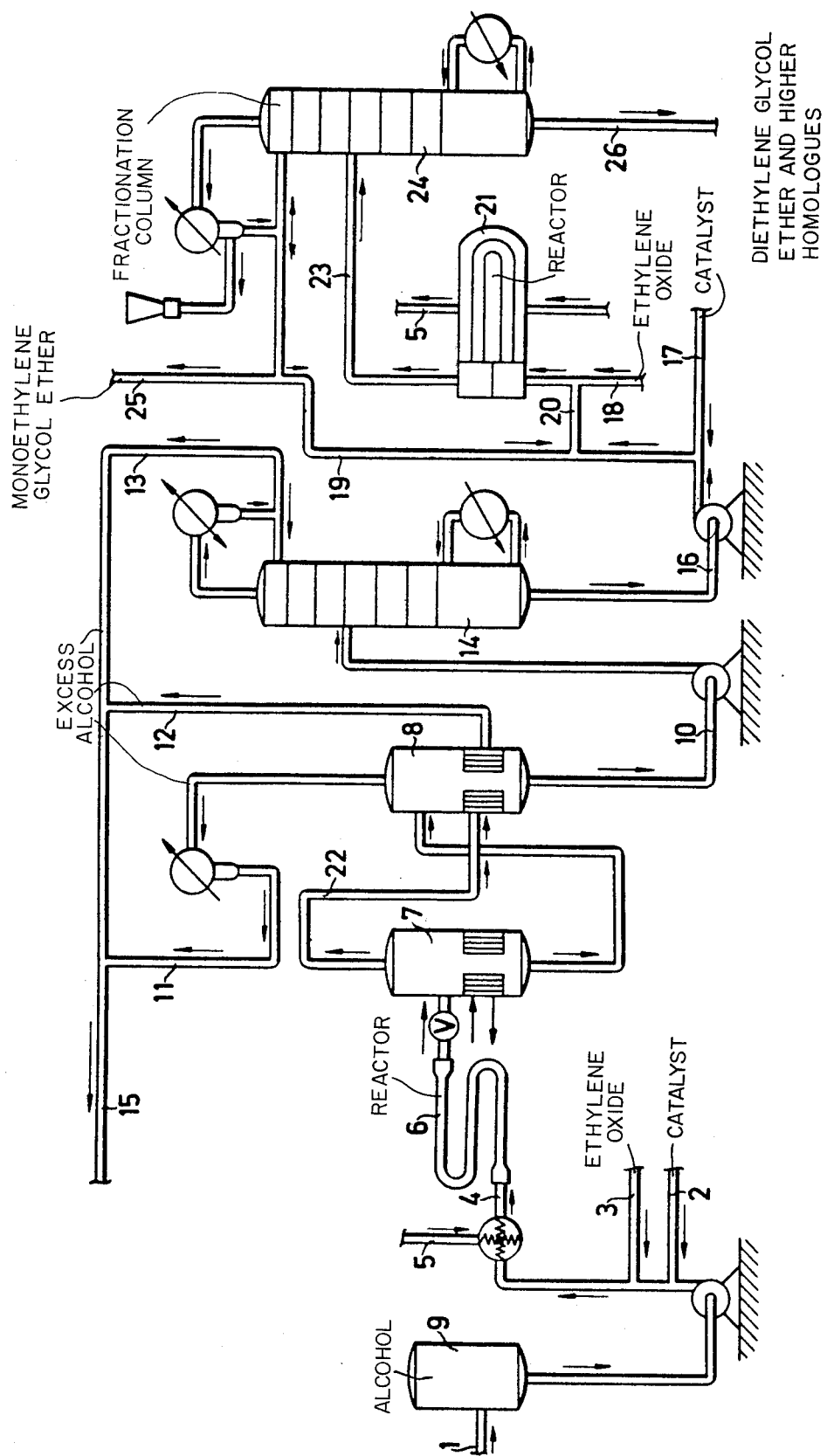

PROCESS FOR THE PRODUCTION OF GLYCOL ETHERS

BACKGROUND OF THE INVENTION

1. Field of the Invention

The present invention relates to an improved process for the production of glycol ethers, and particularly to the production of ethylene glycol ethers by reaction of ethylene oxide with monofunctional aliphatic alcohols. Ethylene glycol ethers are widely used as chemical intermediates and particularly as solvents.

2. Description of the Prior Art

Though various processes are known for the production of ethylene glycol ethers, the only process used industrially involves the reaction of ethylene oxide with monofunctional aliphatic alcohols, such as methanol, ethanol, n-butanol, and isobutanol; see Ullmanns Encyklopaedie der technischen Chemie, 3rd edition, vol. 3, (1953), p. 140. This process is carried out in liquid phase with excess alcohol at high temperatures and pressures.

In general, the reaction is carried out in the presence of suited catalysts, suchc as alkali metal alkoxides, usually sodium alkoxides, sodium hydroxide, tertiary amines, boron trifluoride, antimony pentachloride, and chlorides of bivalent and trivalent metals and the like. Other known processes are carried out in the absence of catalysts so that the problems caused by the separation of the catalyst from the reaction products are avoided; see Ullmanns Encyklopaedie der technischen Chemie, 3rd edition, vol. 3, (1953), p. 141. A further advantage resides in the absence of corrosion due to the catalyst used. In the non-catalytic processes, however, it is necessary to employ more drastic reaction conditions, particularly higher temperatures and pressures than in the catalytic processes.

The reaction of ethylene oxide with monofunctional aliphatic alcohols results in the formation of monoethylene glycol ether, diethylene glycol ether, triethylene glycol ether, and homologues having higher molecular weights. After the reaction is completed, the excess alcohol is removed and the various ethylene glycol ethers produced are then fractionated.

In the known processes the ethylene glycol ethers are produced either continuously or by batchwise operation. In the former case, normally reactors having an elongated shape, generally tubular reactors, are used, and the ethylene oxide may be fed in partly at one or more points located along the body of the reactor.

The problems that arise in the known processes for the production of ethylene glycol ethers by reaction of ethylene oxide with monofunctional aliphatic alcohols are essentially those relating to the reaction yield and the purity of the product obtained and those relating to the composition and distribution of the various ethylene glycol ether homologues in the reaction products. In the processes of the prior art, yields of ethylene glycol ethers higher than 90% with respect to the ethylene oxide fed in and the alcohol converted are rarely obtained. On the other hand, it is important to minimize the formation of triethylene glycol ether and of the higher homologues, since monoethylene glycol and diethylene glycol ethers are the industrially most important products of the homologue series. For this reason, a large excess of the monofunctional aliphatic alcohol is used in the known processes. However, this leads to the formation of reaction products containing predominantly monoethylene glycol ether and only small amounts of diethylene glycol ether, which is undoubtedly a disadvantage, in view of the demand for both of these products.

On the other hand, lower ratios of ethylene oxide to alcohol in the reaction, while increasing the production of diethylene glycol ether as compared to the monoethylene glycol ether, also lead to the formation of products having higher molecular weights that do not find application in practice. In other words, the known processes are not sufficiently flexible to allow the production of monoethylene glycol ether and diethylene glycol ether in the desired ratios, at the same time avoiding the formation of the undesired products having higher molecular weights.

Moreover, in known processes, ethylene glycol ethers of low purity are obtained, particularly because it is difficult to completely remove the excess alcohol from the reaction products.

SUMMARY OF THE INVENTION

It is an object of this invention to provide a simple and economical continuous process for the production of ethylene glycol ethers that allows to avoid or at least to substantially reduce the disadvantages described.

It is a further object of this invention to provide a process for the production of ethylene glycol ethers in high yields and with high selectivities by reaction of ethylene oxide with monofunctional aliphatic alcohols.

Still another object of this invention is to provide a process for the production of monoethylene glycol ether and diethylene glycol ether by reaction of ethylene oxide with monofunctional aliphatic alcohols, which allows substantial reduction of the formation of triethylene glycol ether and of the homologous products having higher molecular weights.

Still another object of this invention is to provide a process that allows to control the content of monoethylene glycol ether and diethylene glycol ether in the products obtained by reaction of ethylene oxide and monofunctional aliphatic alcohols.

Still another object of this invention is to provide a process for the production of ethylene glycol ethers that allows to drastically reduce the amount of alcohol contaminating the monoethylene glycol ether separated by fractionation of the reaction mixture.

The foregoing objects and other which will become apparent from the following description are accomplished in accordance with this invention, generally speaking, by reacting a monofunctional aliphatic alcohol and ethylene oxide in a first reaction stage in a molar ratio of from about 3:1 to 20:1;

separating excess alcohol from the ethylene glycol ethers obtained as the reaction products in the first stage;

reacting the ethylene glycol ethers with ethylene oxide in a molar ratio of from about 1:1 to 10:1 and with monoethylene glycol ether in a second reaction stage;

separating the monoethylene glycol ether and the diethylene glycol ether from the reaction products of the second stage and partly recycling the monoethylene glycol ether to the second stage, maintaining a weight ratio of the discharged fraction to the recycled fraction of from about 0.5:1 to 5:1.

The process of the present invention is characterized in that ethylene oxide and a monofunctional aliphatic alcohols are reacted in a first, adiabatic, reaction stage, whereby high ratios of alcohol to ethylene oxide are maintained;

the products obtained in the first stage are further reacted with monoethylene glycol ether and a further amount of ethylene oxide in a second, isothermal, reaction stage, after previous removal of the excess alcohol;

the second stage is carried out at higher temperatures;

the various ethylene glycol ethers are separated by fractionation of the reaction product discharged from the second stage.

When operating in this way and according to the other conditions that will be defined later, total conversion of the ethylene oxide and a high yield of ethylene glycol ethers with respect to the ethylene oxide fed in and to the alcohol converted are attained. On the other hand, monoethylene glycol ether and diethylene glycol ether are produced in desired ratios within a wide range of values, whereby the formation of triethylene glycol ether and of the homologues having higher molecular weights is substantially reduced. More particularly, in the process of the present invention, yields of ethylene glycol ethers equal to or greater than 98% are attained, while it is possible to vary the molar ratio of monoethylene glycol ether to diethylene glycol ether within a range of from about 30:1 to 1:2, and while keeping the amount of homologues having higher molecular weights at values below 15 parts by weight per 100 parts by weight of the ethylene glycol ethers produced. Moreover, the quantity of alcohol remaining in the monoethylene glycol ether is always less than about 0.05% by weight.

It is thought that the first reaction stage essentially results in the formation of monoethylene glycol ether, while in the second stage part of the monoethylene glycol ether is converted into diethylene glycol either without substantial formation of products having higher molecular weights.

According to the process of the present invention, ethylene oxide and a monofunctional aliphatic alcohol are reacted in a first reaction stage at high temperatures and pressures. Suitable monofunctional aliphatic alcohols, that is, alkanols are methanol, ethanol, n-butanol, isobutanol etc. In particular, molar ratios of alcohol to ethylene oxide of from about 3:1 to 20:1 are maintained in the first reaction stage. The reaction is carried out adiabatically at temperatures of from about 70° to 220°C, at pressures of from about 10 to 50 kg/cm$^2$, with residence times of from about 10 to 240 minutes. In this way, temperatures such as to allow conversions of ethylene oxide of more than 99% are reached in the terminal reaction zone.

The reaction may be carried out in the absence of catalysts, however, it is normally preferred to operate in the presence of substances catalyzing the formation of the ethylene glycol ethers. Suitable catalysts are known in the art, and have been disclosed above. Amount these, the alkali metal alkoxides, which are introduced in the form of alcoholic solutions, are the preferred catalysts. The catalysts are used in quantities of from about 0.01 to 0.2 parts by weight per 100 parts by weight of the alcohol.

The excess alcohol is removed from the product discharged from the first reaction stage, which can be accomplished by two successive operations, specifically by a multi-stage evaporation system followed by rectification. The thus separated alcohol is recycled to the first reaction stage.

According to the process of the present invention, the mixture of ethers remaining after separation of the alcohol is reacted, in a second reaction stage, with monoethylene glycol ether and with a further quantity of ethylene oxide. The ethylene oxide reacts with the glycol ethers, thus noticeably increasing the quantity of diethylene glycol ether without substantial increase in the quantities of the higher homologues.

The small percentages of alcohol that may be present and that originate from the base product of the rectification column are converted practically completely to monoethylene glycol ether, this also being due to the high temperatures in the second reaction stage.

Particularly, in the second reaction stage, the feeds are adjusted so that the molar ratio of ethylene oxide to the effluent from the first stage is in the range of from about 1:1 to 1:10. The reaction is carried out at temperatures of from about 100° to 250°C, at pressures of from about 5 to 2 kg/cm$^2$, and with residence times of from about 20 to 300 minutes. Preferably, alkali metal alkoxides, such as potassium alkoxides, are used as catalysts, the latter being present in quantities of from about 0.02 to 0.2% by weight in the reaction mixture.

The reaction products discharged from the second stage are finally fractionated to obtain the monoethylene glycol ether, the diethylene glycol ether, and the products having higher molecular weights. The monoethylene glycol ether is partly recycled to the second reaction stage. Particularly, a weight ratio between the monoethylene glycol discharged and that recycled in the range of from about 0.5:1 to 5:1 is maintained.

IN THE DRAWING

In the attached drawing, 6 indicates the reactor in which the reaction of ethylene oxide with excess alcohol occurs. Particularly, the alcohol is fed to the reactor 6 from the container 9, the alcohol consisting partly of alcohol recycled from the fractionation and partly of fresh alcohol (pipes 1 and 15). Moreover, the catalyst is fed through pipe 2, while the ethylene oxide is fed through pipe 3. The resulting mixture is preheated to the reaction temperature in the heat exchanger 4. The reactor 6 is of the tubular adiabatic type with plug flow. The diameter of the tube is chosen so as to give Reynolds numbers greater than 100,000 for predicted linear velocities of 10 metres/minute. The excess alcohol is separated from the products discharged from the reactor 6. The attached drawing illustrates a preferred embodiment in which the excess alcohol is removed by means of two evaporation stages (evaporators 7 and 8) followed by a rectification stage (column 14). In this preferred embodiment, the evaporator 7 is heated by means of steam, while the alcohol vapour discharged through pipe 22 is used for heating evaporator 8, an economic advantage being gained in this way.

In order to remove the last traces of alcohol the concentrate is passed to the rectification column 14 through pipe 10. The alcohol recovered through the pipes 11, 12, and 13 is recycled to the container 9 through pipe 15. The ethylene glycol ethers contaminated by small amounts of alcohol are recovered through pipe 16, and are mixed with further catalyst fed through pipe 17. Moreover, ethylene oxide and recycled monoethylene glycol ether are fed through pipes 18 and 19, respectively. The mixture thus obtained in pipe 20 is passed to the isothermic reactor 21, which consists of a bundle of U tubes immersed in a boiling liquid bath. The apparatus is similar to a reboiler of the kettle type, the diameter of the tubes being such as to give Reynolds numbers greater than 10,000 for predicted linear velocities equal to about 15 metres/minute. The vapours of the cooling liquid used in the isothermic reactor 21 may be passed to the preheater 4 through pipe 5.

The reaction mixture discharged through pipe 23 is passed to the fractionation column 24, at the top of which the monoethylene glycol ether is separated. The higher homologues are recovered at the base of column 24 through pipe 26. The monoethylene glycol ether is partly recycled to the reactor 21 through pipe 19 and for the rest drawn off through pipe 25.

The invention is further illustrated but is not intended to be limited by the following example.

EXAMPLE

In the plant shown in the attached drawing, sodium methoxide is added through pipe 2 to a stream of alcohol coming from the tank 9 whereby a weight ratio of sodium methoxide to methanol of about 1:1000 is maintained. Ethylene oxide is fed through pipe 3 is a quantity such as to ensure a weight ratio of methanol to ethylene oxide of about 9:1. The resulting mixture is heated to a temperature of about 90°C in the heat exchanger 4 by the steam fed through pipe 5 and is then passed to the plugflow adiabatic reactor 6, operated at a pressure of about 30 kg/cm². The linear velocity of the mixture in the reactor 6 is about 10 metres/minute, the Reynolds number is about 150,000, and the residence time is about 60 minutes. Under these conditions, a conversion of the ethylene oxide of 99.9% is attained and the weight distribution of the glycol ethers formed is as follows: monoethylene glycol ether 91.5%, diethylene glycol ether 6%, triethylene glycol ether 2%, products of higher molecular weight 0.5%. The reaction mixture drawn off from the reactor 6 and having a temperature of about 150°C, is passed to the multistage evaporator system (7 and 8), where it is evaporated to obtain a concentrate containing about 45% by weight of glycol ethers. The concentrate obtained is fed to the rectification column 14 through pipe 10, the column having 18 plates and being operated at about 1.5 kg/cm² and with a reflux ratio of about 1.

The alcohol discharged at the top of the column 14 through pipe 13 and containing about 1% of monoethylene glycol ether is recycled to the tank 9 through pipe 15. The alcohol streams recovered through pipes 11 and 12 are also recycled. The glycol ethers containing about 0.2% by weight of methanol are recovered at the base of the column 14 through pipe 16. Potassium methoxide is added to the glycol ethers through pipe 17 at a weight ratio of potassium methoxide to glycol ethers of about 1:500, and monoethylene glycol ether is added through pipe 19 in a quantity of one part by weight per part by weight of the glycol ethers carried through pipe 16. In this way, a mixture containing 96 mole-% of monoethylene glycol ether, 2 mole-% of diethylene glycol ether, and 0.4 mole-% of triethylene glycol ether is obtained in pipe 20. Ethylene oxide is added to this mixture through pipe 18 in a molar ratio of ethylene oxide to glycol ethers of about 1:4. The resulting mixture is fed to the isothermal reactor 21 consisting of a bundle of U tubes maintained at a temperature of about 150°C by means of an evaporating bath. The vapour of the diathermic fluid in pipe 5 is used as the heating means in the preheater 4. The reactor 21 is operated at a pressure of about 10 kg/cm² and with a residence time of about 90 minutes, the linear velocity of the mixture being about 15 metres/minutes, with a Reynolds number of about 30,000. Under these conditions a conversion of the ethylene oxide of 99.5% is attained. The reaction mixture is then fed to the fractionation column 24 through pipe 23, the column having 25 plates and being operated at a pressure of about 200 mmHg and with a reflux ratio of about 0.5. Monoethylene glycol ether having a purity of 99.9% and containing about 0.02% by weight of methanol, the remainder consisting of diethylene glycol ether, is withdrawn from the top of the column 24. The monoethylene glycol ether from the top of the column 24 is partly recycled to the reactor 21 through pipe 19 whereby a weight ratio of the fraction discharged through pipe 25 to the recycled fraction of about 1.05 is maintained.

The base products consisting of diethylene glycol ether (80% by weight) and triethylene glycol ether (18% by weight) are discharged from the column 24 through pipe 26. The weight ratio of the product discharged through pipe 26 to that discharged through pipe 25 is about 7:6.

The product discharged through pipe 26 is passed to a subsequent column (not shown) in order to separate the diethylene glycol ether.

What we claim is:

1. An improved process for the production of ethylene glycol ethers by the reaction of ethylene oxide with $C_1$–$C_4$ aliphatic alcohols, wherein the improvement comprises contacting a $C_1$–$C_4$ alkanol and ethylene oxide in a first reaction stage, under adiabotic conditions, in a molar ratio of from about 3:1 to 20:1, at a temperature of from about 70° to 220°C., at a pressure of from about 10 to 50 Kg/cm²;

evaporating excess alcohol from ethylene glycol monoalkyl ethers obtained as the reaction products in the first stage;

contacting the ethylene glycol monoalkyl ethers with ethylene oxide in a molar ratio of from about 1:1 to 10:1 and with monoethylene glycol monoalkyl ether in a second reaction stage at a temperature of from about 100° to 250°C., under isothermal conditions, at a pressure of from about 5 to 20 kg/cm²;

fractionating monoethylene glycol monoalkyl ether and diethylene glycol monoalkyl ether from the reaction products of the second stage and partly recycling the monoethylene glycol monoalkyl ether to the second stage, and discharging the remainder of the monoethylene glycol monoalkyl ether, maintaining a weight ratio of discharged fraction to the recycled fraction of from about 0.5:1 to 5:1.

2. A process as recited in claim 1, wherein the first reaction stage is carried out with residence times of from about 10 to 240 minutes.

3. A process as recited in claim 2, wherein the second reaction stage is carried out with residence times of from about 20 to 300 minutes.

4. A process as recited in claim 2, wherein the $C_1$–$C_4$ aliphatic alcohol is selected from the group consisting of methanol, ethanol, butanol, and isobutanol.

5. A process as recited in claim 2, wherein the first and second reaction stages are carried out in the presence of catalysts, preferably of alkali metal alkoxides.

6. A process as recited in claim 5, wherein the catalyst is used in the first reaction stage in an amount of from about 0.01 to 0.2 parts by weight per 100 parts by weight of the $C_1$–$C_4$ aliphatic alcohol.

7. A process as recited in claim 5, wherein the catalyst is used in the second reaction stage in an amount of from about 0.02 to 0.2% by weight of the reaction mixture.

\* \* \* \* \*